US00PP36982P2

(12) United States Plant Patent
Holtmaat

(10) Patent No.: US PP36,982 P2
(45) Date of Patent: Sep. 23, 2025

(54) ***DELPHINIUM* PLANT NAMED 'Dellas 812'**

(50) Latin Name: *Delphinium elatum*
Varietal Denomination: Dellas 812

(71) Applicant: Henricus Maria Joseph Holtmaat, Zuidwolde (NL)

(72) Inventor: Henricus Maria Joseph Holtmaat, Zuidwolde (NL)

(73) Assignee: AB-KWEKERSRECHTEN B.V., Zuidwolde (NL)

( * ) Notice: Subject to any disclaimer, the term of this patent is extended or adjusted under 35 U.S.C. 154(b) by 0 days.

(21) Appl. No.: 19/054,797

(22) Filed: Feb. 15, 2025

(30) Foreign Application Priority Data

Dec. 3, 2024 (QZ) ..... PBR 2024/2631

(51) Int. Cl.
*A01H 5/02* (2018.01)
*A01H 5/00* (2018.01)
*A01H 6/72* (2018.01)

(52) U.S. Cl.
USPC ..... Plt./423
CPC ..... *A01H 6/72* (2018.05); *A01H 5/00* (2013.01)

(58) Field of Classification Search
USPC ..... Plt./423
See application file for complete search history.

(56) References Cited

U.S. PATENT DOCUMENTS

PP32,994 P2 * 4/2021 Noordhuis ..... Plt./423
PP33,009 P2 * 4/2021 Noordhuis ..... A01H 6/72 Plt./423

* cited by examiner

*Primary Examiner* — Susan McCormick Ewoldt
(74) *Attorney, Agent, or Firm* — Penny J. Aguirre

(57) ABSTRACT

A new cultivar of *Delphinium* plant named 'Dellas 812' that is characterized by its compact, dense, and a neat plant habit and its flowers that are intense violet to violet-blue in color with contrasting white anthers.

3 Drawing Sheets

Botanical classification: *Delphinium elatum.*
Variety denomination: 'Dellas 812'.

BACKGROUND OF THE INVENTION

The present invention relates to a new and distinct cultivar of *Delphinium elatum* will be referred to hereafter by its cultivar name, 'Dellas 812'. 'Dellas 812' is a new herbaceous perennial for use as an ornamental landscape plant.

'Dellas 812' originated as a seedling that arose from seed planted from open pollination of unnamed and unpatented plants of *Delphinium elatum* from the Inventor's breeding program in Zuidwolde, The Netherlands in July of 2022. The collected seeds were combined prior to sowing and therefore the parentage is unknown.

Asexual propagation of the new cultivar was first accomplished by the Inventor by tissue culture using meristematic tissue in Heerhugowaard, The Netherlands in January 2023. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Dellas 812' as a unique cultivar of *Delphinium.*

1. 'Dellas 812' exhibits a compact, dense, and a neat plant habit.

2. 'Dellas 812' exhibits flowers that are intense violet to violet-blue in color with contrasting white anthers.

'Dellas 812' can be compared to the *Delphinium* cultivars 'ET DLP 17-03' (U.S. Plant Pat. No. 33,009) and 'ET DLP 17-11' (U.S. Plant Pat. No. 32,994). 'ET DLP 17-03' is similar to 'Dellas 812' in foliage color. 'ET DLP 17-03' differs from 'Dellas 812' in having a taller plant height and flowers that are light purple in color. 'ET DLP 17-11' is similar to 'Dellas 812' in plant habit and foliage color. 'ET DLP 17-11' differs from 'Dellas 812' in having a taller plant height and flowers that are much lighter violet to violet-blue in color.

BRIEF DESCRIPTION OF THE DRAWINGS

The accompanying color photographs illustrate the overall appearance and distinct characteristics of the new *Delphinium.* The photographs were taken of a four-month-old plant as grown outdoors and in an unheated greenhouse (6 weeks) in a 19-cm container in Heerhugowaard, The Netherlands.

The photograph in FIG. 1 provides a side view of the overall plant habit of 'Dellas 812' in bloom.

Figure 1:
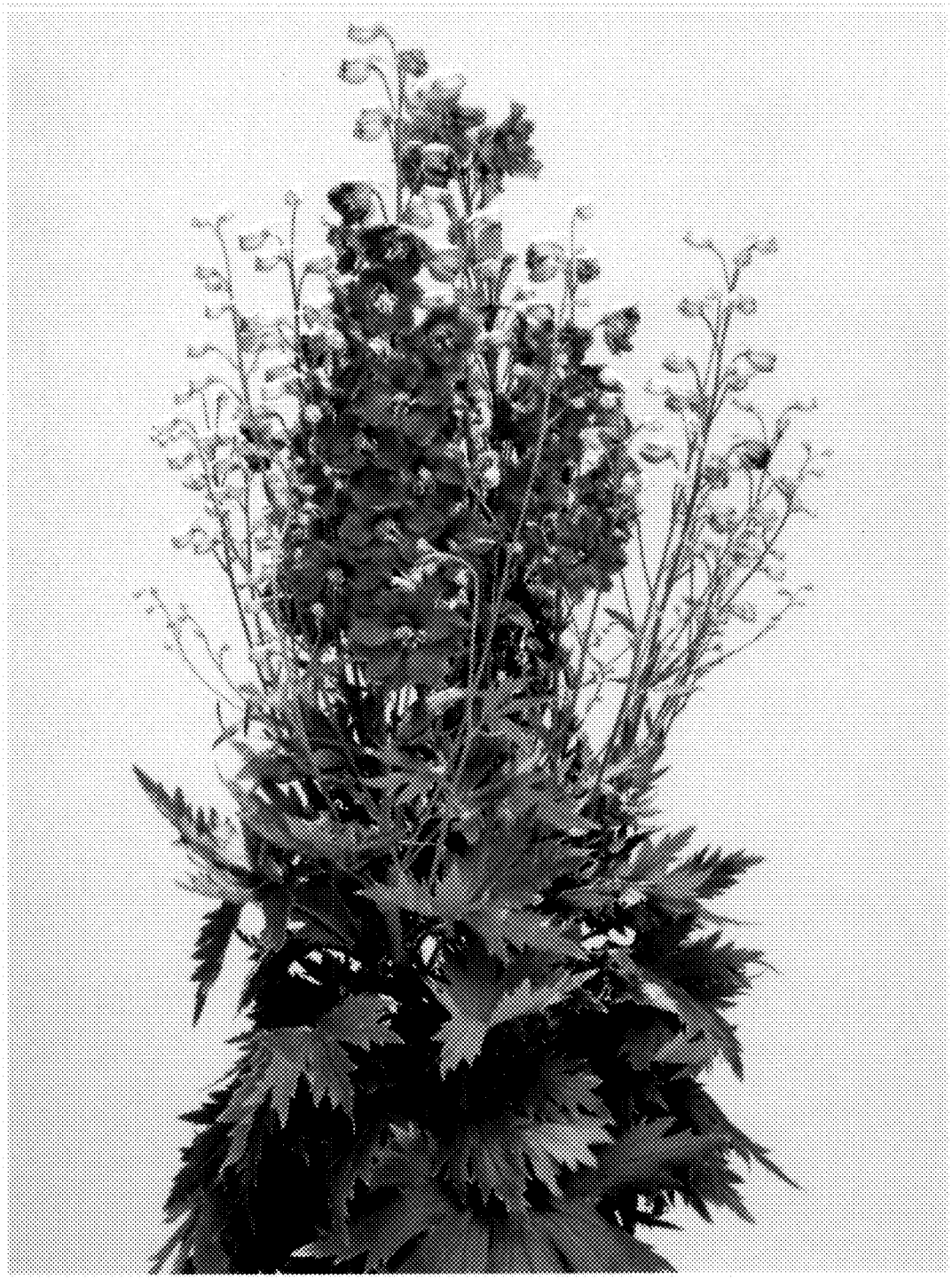
Figure 2:
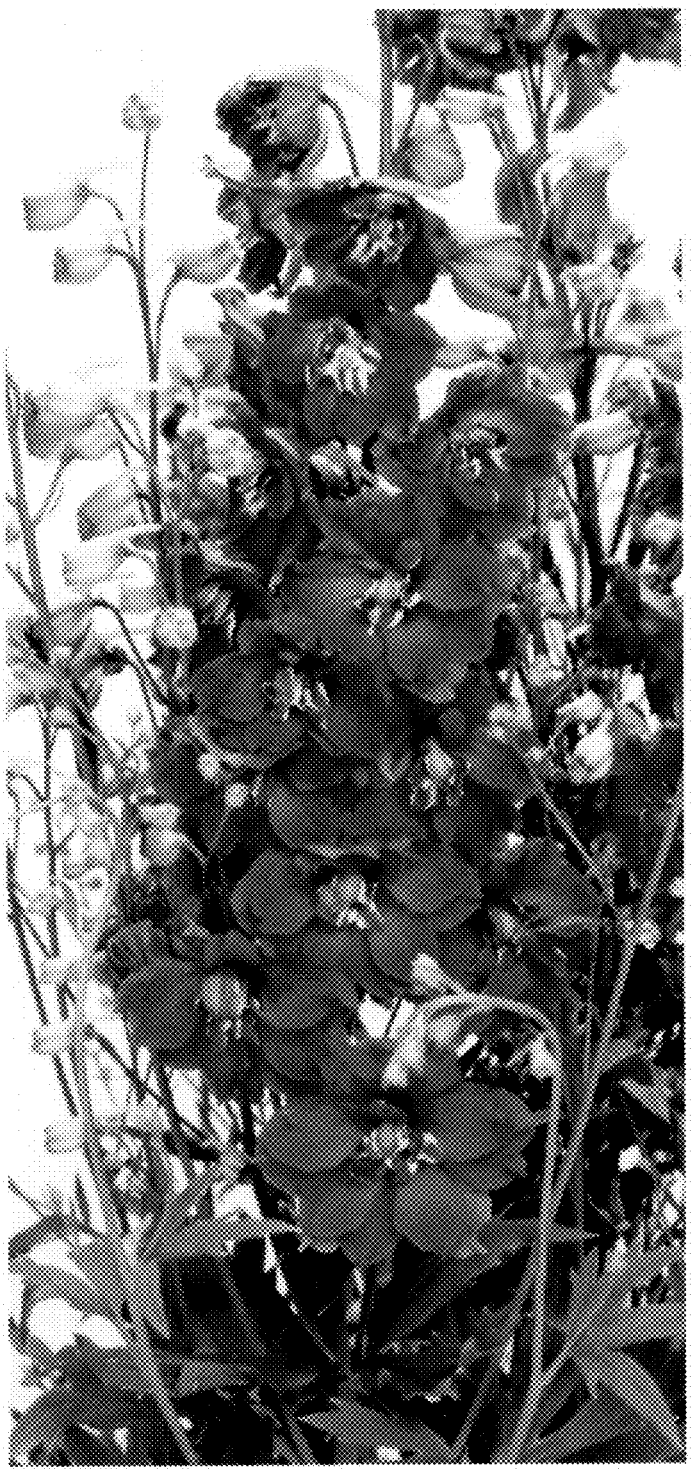

The photograph in FIG. 2 provides a close-up view of an inflorescence of 'Dellas 812'.

Figure 3:
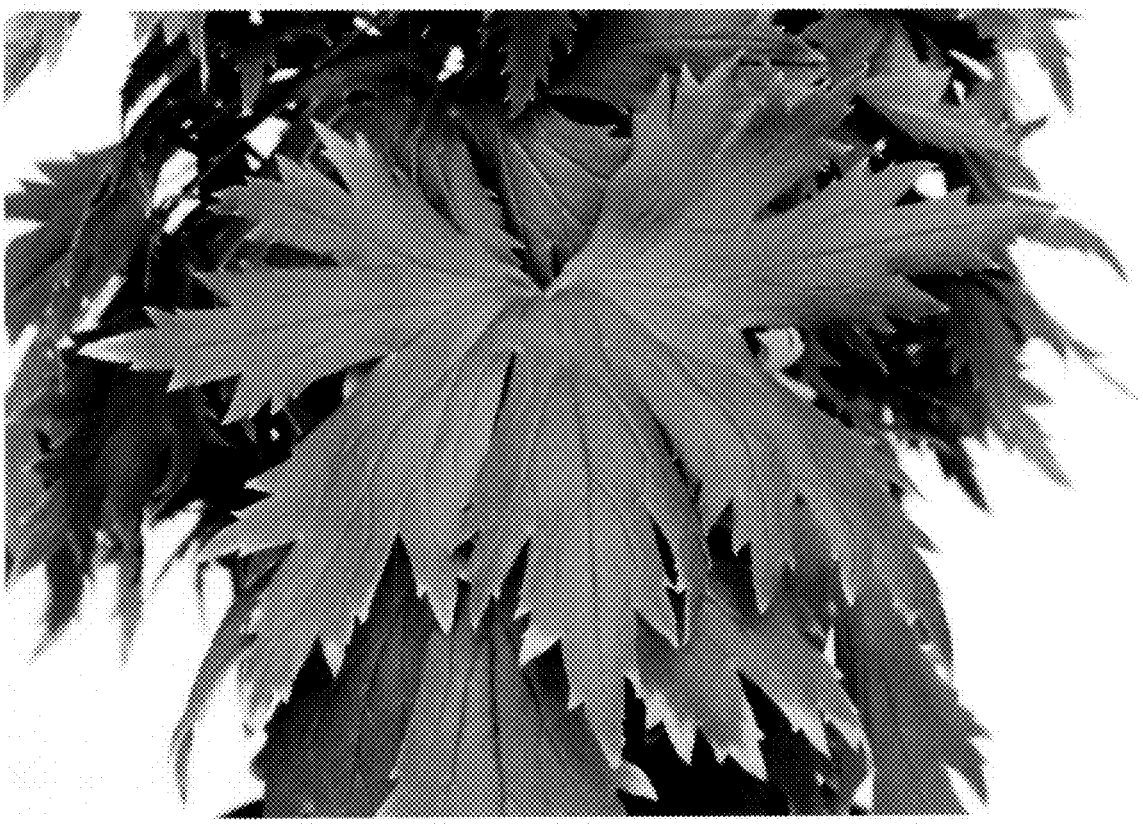

The photograph in FIG. 3 provides a close-up view of a leaf of 'Dellas 812'.

The colors in the photographs are as close as possible with the photographic and printing technology utilized and the color values cited in the Detailed Botanical Description accurately describe the colors of the new *Delphinium*.

DETAILED BOTANICAL DESCRIPTION

The following is a detailed description of four-month-old plants as grown outdoors and in an unheated greenhouse (6 weeks) in 19-cm containers in Heerhugowaard, The Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period*.—July to August in The Netherlands.

*Plant type*.—Herbaceous perennial.

*Plant habit*.—Very compact, upright and naturally rounded, dense.

*Plant size*.—An average of 42.9 cm from soil level to top of foliar plane, 60.3 cm from soil level to top of floral plane, 49 cm in spread as a 4-month-old plant as grown in a container.

*Hardiness*.—At least in U.S.D.A. Zones 5 to 9.

*Diseases and pests*.—No susceptibility and resistance to diseases or pests has been observed.

*Propagation*.—Tissue culture.

*Root description*.—Fibrous.

*Root development*.—3 weeks to initiate roots, 5 weeks to produce a rooted cutting.

*Growth rate*.—Moderate.

Branch description:

*Branch shape*.—Round and very slightly angled, 5-sided.

*Branch color*.—Young; 146D, mature; 146C, axially striped 146A.

*Branch strength*.—Strong.

*Branch size*.—Up to 23 cm in length and 1 cm in diameter.

*Branch surface*.—Slightly glossy, covered with a thin waxy layer that is 145B in color, bases of stems (lower 5 cm) moderately to densely pubescent; average length of hairs 0.2 cm, 198D in color.

*Branch aspect*.—Lateral stems held upright in an average angle of 15° to vertical.

*Branch internode length*.—Average of 1.3 cm.

*Branching*.—4 flowering stems; no branches or lateral branches, flowering stems grow from the base.

Foliage description:

*Leaf shape*.—Palmate, broadly reniform in outline.

*Leaf division*.—Simple.

*Leaf base*.—Broadly and shallowly hastate to short attenuate, lobes free.

*Leaf apex*.—Narrow acute.

*Leaf fragrance*.—None.

*Leaf venation*.—Laciniate, upper surface; 144A, lower surface; 146D.

*Leaf margins*.—Coarsely serrate, deep sinuses, divergent.

*Leaf arrangement*.—Alternate.

*Leaf attachment*.—Petiolate.

*Leaf surface*.—Upper surface slightly pubescent, slightly glossy, lower surface glabrous and matte.

*Leaf size*.—15.6 cm in length and an average of 21.5 cm in width.

*Leaf quantity*.—An average of 18 per main stem.

*Leaf color*.—Young upper surface; 143A, young lower surface; 138B, mature upper surface; a blend of NN137A and 147A, mature lower surface; 147B.

*Petioles*.—An average of 11.7 cm in length and 4 mm in diameter, both surfaces 144A in color, strong, surface is smooth, glabrous appearance, moderately glossy with a waxy luster, young and mature sparsely pubescent with very short hairs; average of 1.5 mm in length, N155A in color.

Inflorescence description:

*Inflorescence type*.—Axillary or terminal raceme.

*Inflorescence size*.—35.5 cm in height, 11.3 cm in diameter.

*Flower fragrance*.—None.

*Lastingness of flowers*.—An average of 10 days, self-cleaning.

*Flower buds*.—Broad oblong in shape, top flattened, average of 2.5 cm in length and 1cm in diameter, color; 145B to 145C, upper side flushed with N187C, tinged at the tip 137C.

*Flower aspect*.—Outwardly.

*Flower quantity*.—Average of 36 flowers per inflorescence, 16 inflorescences per secondary inflorescence, 140 flowers per plant.

*Flower type*.—Rotate, semi-double.

*Flower surface*.—All surfaces glabrous and matte.

*Flower size*.—An average of 5.4 cm in height, 6.2 cm in diameter, 3.7 cm in depth.

*Peduncles*.—Average of 46.4 cm in length, 5 mm in diameter, 146A in color, held in a vertical angle, strong, surface is smooth and glabrous, moderately glossy, covered with a very thin waxy layer 148C in color.

*Pedicels*.—Average of 5.1 cm in length, 1 mm in diameter, a blend of 143A and 146A in color, held in a 40° angle, moderately strong, surface is smooth and glabrous, glossy, covered with a very thin waxy layer, 148C in color.

*Calyx*.—Rotate in shape, an average of 3.7 cm in length and 6.2 cm in diameter.

*Sepals*.—None present.

*Petals*.—None present.

*Tepals*.—Average of 5, rotate, one dorsal tepal, 2 upper lateral tepals and 2 lower lateral tepals, 1 whorl, broadly elliptic in shape, entire margins, slightly undulated, apex short and bluntly aristate, base is broadly cuneate, an average of 3.2 cm in length, lower lateral tepals 3.3 cm in length, 2.8 cm in width, color: when opening upper surface; dorsal tepal N89C and N89D, lower half and base; N87C and N87D, upper lateral tepals N87A, top 93A, base N87D, lower lateral tepals N87A, flushed with N95D, when opening lower surface; dorsal tepal 93C and 93D, top 137A, upper lateral tepals N87A, center (central band); 146D, with a small blotch near the top 146B, when fully open upper surface; dorsal tepal 94A, lower half fading towards the base N87B to N87D, upper lateral tepals N87A, fading at the base to N82B, lower lateral tepals 96B, fading at the base; N87D, lower lateral tepals 90A, fading in center (central band) 146D, small blotch near the top 146A, when fully open lower surface; dorsal tepal 93C, fading towards the base to N87D, upper lateral tepals N87A, fading lighter at the base N87C, tepal with a yellow-green central band; lighter than 146D, and a small yellow-green blotch near the top; 146B, lower lateral tepals 93B, flushed with N87B and N87C, central band lighter than 146D, and a blotch near the top 146B.

*Tepaloids*.—Rotate, total of 16; 8 outer 8, 8 inner, average of 2 whorls (guard tepaloids, honey tepaloids), outer tepaloids; elliptic to narrowly elliptic, average of 3cm in length, 1.7 cm in width, apex abruptly acute, cuneate base, surfaces are glabrous, slightly velvety, very slightly glossy, undulations medium, color; when opening upper surface N88A, central band lighter N87B, fading lighter towards the base to N87D, when opening lower surface; N88B, central band and base lighter 85B, and with a small blotch near the top 146D, when fully open upper surface N87A and N88A, fading lighter towards the base N87C, when fully open lower surface N88B and N89C, fading towards the base; N87C, inner tepaloids; oblanceolate to near narrow spathulate in shape, average of 1.9 cm in length, 6.5 mm in width, apex obtuse to finely praemorse, narrow cuneate base, surfaces are glabrous, slightly velvety, very slightly glossy, undulations low, color; when opening upper surface wide portion N88A, fading towards the narrow part to N82B, margins 155C, narrow part 145A, when opening lower surface; wide part N88B, central band and base 85B with a small blotch near the top 146D, margins 155C, narrow part 145A, when fully open upper surface wide part N89C, fading towards the narrow part a blend of N87C and N87D, margins 155C, narrow part 145B, when fully open lower surface wide part N89D, central band a blend of NB178B and N187C, margins 157D, narrow part 145B.

*Tepal spurs*.—Dorsal tepal with 1 spur, 2 cm in length, 3 mm in diameter, narrow oblong in shape, obtuse apex, base broadly cuneate, surfaces smooth, glabrous, slightly glossy, color; N187B, apex 146C to 146D.

*Bracts*.—2 bracts are nearly opposite placed near the distil end of the pedicel, linear in shape, narrowly acute apex, narrowly cuneate base, 1.2 cm in length, 1.5 mm in width, surfaces are smooth and glabrous, margins are sparsely covered with short pubescent hairs; 1 mm in length, 137A to 137B in color.

Reproductive organs:

*Gynoecium*.—4 pistils, 2 mm in length, style; an average of 2 mm in length, 145D in color, stigma; pointed, 1 mm in length, 0.5 mm in diameter, NN155A in color, ovary; 150C in color.

*Androecium*.—Stamens; 30, filament; 7 mm in length, flattened at the base, 157D in color, anther; oblong in shape, 2 mm in length, 0.1 mm in diameter, N148C in color, pollen; low in quantity, 155A in color.

*Fruit and seed*.—No seeds or fruit observed to date.

It is claimed:

1. A new and distinct cultivar of *Delphinium* plant named 'Dellas 812' as herein illustrated and described.

* * * * *